United States Patent
Lee et al.

(10) Patent No.: US 6,236,882 B1
(45) Date of Patent: May 22, 2001

(54) NOISE REJECTION FOR MONITORING ECG'S

(75) Inventors: Brian B. Lee, Golden Valley; Michael R. Kane, Shoreview, both of MN (US); Gregg Turi, Budd Lake, NJ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/353,167

(22) Filed: Jul. 14, 1999

(51) Int. Cl.$^7$ .............. A61B 5/0402; A61B 5/0432; A61B 5/0452; A61B 5/0456
(52) U.S. Cl. ................ 600/509; 600/521; 600/523
(58) Field of Search ............................. 607/509, 521, 607/523

(56) References Cited

U.S. PATENT DOCUMENTS

| | | |
|---|---|---|
| 4,223,678 | 9/1980 | Langer et al. . |
| 4,407,288 | 10/1983 | Langer et al. . |
| 4,556,063 | 12/1985 | Thompson . |
| 4,974,589 | 12/1990 | Sholder . |
| 5,188,105 | 2/1993 | Keimel . |
| 5,193,550 * | 3/1993 | Duffin ........................ 128/697 |
| 5,313,953 | 5/1994 | Yomtov et al. . |
| 5,331,966 * | 7/1994 | Bennett et al. ................ 607/28 |
| 5,339,824 | 8/1994 | Engira et al. . |
| 5,404,887 | 4/1995 | Prather et al. . |
| 5,464,431 | 11/1995 | Adams et al. . |
| 5,464,434 | 11/1995 | Alt . |
| 5,518,001 | 5/1996 | Snell . |
| 5,759,196 | 6/1998 | Hess et al. .................... 607/14 |
| 5,776,168 * | 7/1998 | Gunderson ...................... 607/27 |

OTHER PUBLICATIONS

Pace Dec. 1992 vol. 15 (15:588) by Leitchetal Subcutaneous Bipolar "Pseudo–ECG" Recording Using an Implantable Montotring System and at Chaired Poster Presentation of the North American Society of Pacing and Electrogphysiology (NASPE).

Arrthmia Detectoin Program for an Ambulatory ECG Monitor by Mueller Copyright 1978, ISA ISBN 876645.

* cited by examiner

Primary Examiner—Carl H. Layno
(74) Attorney, Agent, or Firm—Michael B. Atlass; Harold R. Patton

(57) ABSTRACT

An implantable medical device which preferably has a segmented looping memory for storing triggered physiologic events also has autotriggers to record the ECGs and any other relevant physiologic signals occurring during triggering events. The problem is that in the far field R-wave sensing is difficult because of noise. Denial and extensible accommodation periods are introduced into the R-wave sensing registration for triggering data storage. If the event is sensed during an accommodation period the sense will not add an R-wave sense to the trigger's count of R-waves. It may cause resetting of the trigger count in some circumstnaces. Typical triggering events may include arrhythmia's and syncopal events. Preferably the device can function without a microprocessor. An outside device or other patient activated manual trigger may be included. Auto triggers and manually set triggers may be of different sizes. Electrode spacing can be critical. Additional sensors may be provided to the device. Preferred communications with the device is through telemetry such as is used for pacemakers and other implanted devices.

20 Claims, 15 Drawing Sheets

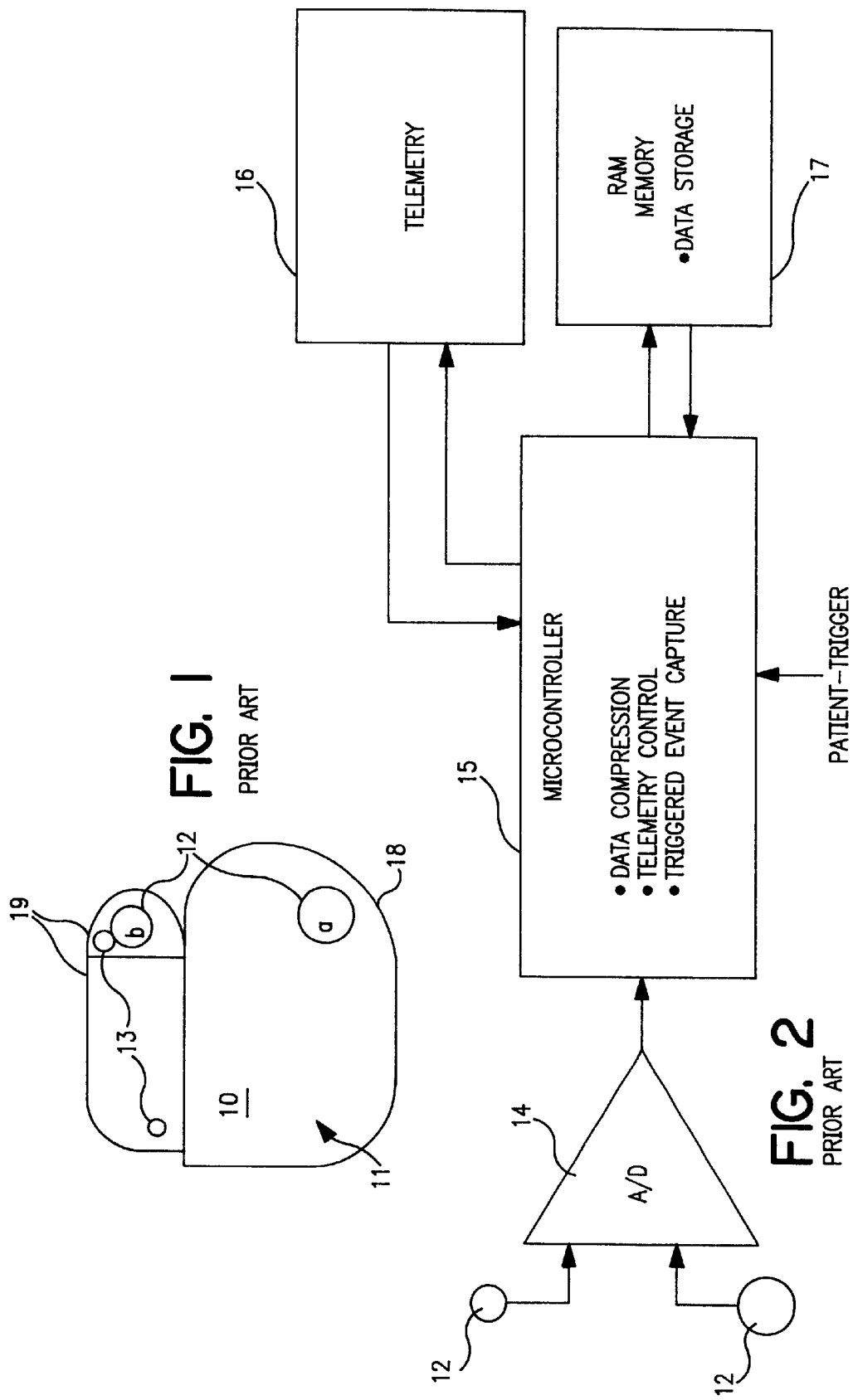

NOISE REJECTION FOR MONITORING ECG'S

This invention relates to an implantable monitoring device for sensing physiologic events, preferably with minimally invasive intrusion into an animal or patient body, but which can be used with various implantable devices that provide long term monitoring of ElectroCardioGrams (ECG's). More particularly this invention relates to methods and devices for rejecting noise common in such monitoring.

BACKGROUND OF THE INVENTION

In the monitoring of long term ECGs for features indicating intermittent heart irregularities, syncopal events and the like, minimally invasive monitors like the Reveal (TM) electrocardiogram event recorder manufactured by Medtronic, Inc. have proven to be useful, and now appear to be accepted by a segment of the medical community for use in diagnosing patient problems like fainting. However, particularly when the device employs automatic arrhythmia detection triggers to activate the storage of a segment of the ECG, the presence of noise in the ECG signal channel may trigger activation's inappropriately, causing the memory to become full of unwanted portions of the cardiac electrogram that may be of little to no use in diagnosing the patient condition.

Accordingly, we have developed a method along with apparatus to employ it, for eliminating a high proportion of the noise in the signal which might otherwise cause improper activation of automatic electrocardiogram (ECG) storage.

Monitoring can be done using implantable pulse generators such as pacemakers and other heart stimulating devices or devices with leads in the heart for capturing physiologic parameters, including the ECG. However, the expense and risk from implanting a pacemaker or changing out one without these functions is something both patients and physicians would prefer to avoid. Such devices, in addition to performing therapeutic operations, may monitor and transmit cardiac electrical signals (e.g., intracardiac electrograms) to an external diagnostic device typically with leads fixed in the patient's heart, to observe electrical activity of a heart. It is common for implanted cardiac stimulation devices to send intracardiac EGM (electrocardiograms taken from in the heart) signals to a monitoring device, such as an external programmer, to allow a user to analyze the interaction between the heart and the implanted device. Often the user can designate that the communication from the implantable device to the programmer include a transmission of codes which signal the occurrence of a cardiac event such as the delivery of a stimulation pulse or a spontaneous cardiac depolarization.

For example, U.S. Pat. No. 4,223,678, (incorporated herein by this reference in its entirety) entitled "Arrhythmia Recorder for Use with an Implantable Defibrillator", issued to Langer et al. on Sep. 23, 1980, discloses an arrhythmia record/playback component within an implantable defibrillator. ECG data is converted from analog to digital (A/D) form and stored in a first-in, first-out memory. When the defibrillator detects an arrhythmia event, it disables the memory so that no further ECG data is recorded in the memory until a command is received from an external monitoring device. This command requests the implantable defibrillator to transmit the stored ECG data to the monitoring device via telemetry. Langer et al. in U.S. Pat. No. 4,407,288, (also incorporated by reference herein) entitled "Implantable Heart Stimulator and Stimulation Method", issued Oct. 4, 1983, discloses a programmable, microprocessor based implantable defibrillator which senses and loads ECG data into a memory via a direct memory access operation. A processor analyzes this ECG data in the memory to detect the occurrence of an arrhythmia event afflicting a patient's heart. Upon such an event, the defibrillator may generate a therapy to terminate the arrhythmia event and store the ECG data sequence of the event, for transmission to an external monitoring device and later study. In normal circumstances, when no arrhythmia event is occurring, the defibrillator continuously overwrites the ECG data in the memory.

U.S. Pat. No. 4,556,063, (too, incorporated herein by this reference) entitled "Telemetry System for a Medical Device", granted to D. L. Thompson et al, 1985, teaches a pulse interval telemetry system capable of transmitting analog data, such as sensed intracardiac electrogram signals, without converting analog data to a digital numeric value. The Thompson et al. telemetry system is capable of sequentially transmitting both digital and analog data, individually and serially, in either an analog or a digital format, to a remote receiver. The features and capabilities of these pacemaker/defibrillator devices is now well known, but the problems in long term monitoring for events and adequate recordation remain.

Other background includes an article in the December 1992 Vol. 15 edition of PACE (15:588), a feasibility study for implantable arrhythmia monitors and reported by Leitch et al. Subcutaneous, Bipolar "Pseudo-ECG" Recordings using an Implantable Monitoring System and at chaired poster presentation of the North American Society of Pacing and Electrophysiology (NASPE).

Further, a leadless implantable sensor for cardiac emergency warning was described in U.S. Pat. No. 5,404,887 issued to Knowlan et al. which detects heart events through impedance measurement sensed using a coil. See also Yomtov et al, U.S. Pat. No. 5,313,953 (incorporated herein by this reference) which describes (in FIG. 26) a large but leadless implant.

With sufficient hardware and connections to the body, numerous other physiologic parameters may be sensed as is pointed out in U.S. Pat. No. 5,464,434 issued to Alt and U.S. Pat. No. 5,464,431 issued to Adams et al. (both also incorporated herein by this reference).

Nevertheless there is still a need to reject the noise inherent in the ECG signals for automatic detection of arrhythmias. It is particularly problematic to detect abnormal ECGs taken in the "far field" of the subcutaneous electrodes used in the Reveal(TM) and other under-the-skin long term monitors.

While 'blanking' and 'refractory' periods are commonly used in pacemakers and implantable cardiodefibrillators (ICD's) today, their application to implantable devices which do not deliver therapy, and to ECG storage automatic triggers and their use in far field ECG recording has not been seen. Such blanking and refractory periods do eliminate or limit the sensing abilities of the implanted medical devices in which they are used, however. Examples of such periods in the therapy delivery device art include U.S. Pat. No. 5,759,196, Hess, et al., U.S. Pat. No. 5,188,105, issued to Keimel, and U.S. Pat. No. 4,974,589, issued to Sholder. All these patents are incorporated by this reference in their entireties by this reference thereto. Nevertheless, none of these use such periods to exclude signals from the far field ECG, which they do not have the capacity to record.

Picking up good ECG signals in the far field but within the body is fraught with noise problems. (To clarify, by "far field" we mean ECG measurements taken outside the heart but under the skin. This commonly may also be called subcutaneous ECG measurement.)

Particularly in looping ECG recording systems which automatically detect arrhythmias according to specific arrhythmia detection criteria and retain segments of the ECG in recorded data memories as well as in other ECG recording systems, there are several areas in which false detects can fill up the memory for data storage with unwanted data. ('False detects' here means that a predetermined number of QRS segments or R-waves has been detected over an appropriately predetermined trigger time to set off a trigger criterion that is monitoring the detection of R-waves and sending the data to the trigger monitoring circuit. The trigger circuit then sets off a detect signal, forcing the implantable recorder to record a segment of the ECG into the memory of the implantable medical device).

First among likely noise sources is false detection's of noise leading to false Tachy detects (i.e. inappropriate detections of an electrocardiogram segment). Muscle noise (EMG noise) can easily dominate the signal of the Electrocardiogram. While it is impossible to filter out all of this noise and it is particularly susceptible to noise in the subcutaneous area where the leads of the small ECG implantable monitor are usually located. This noise will generally be broad band and subsumes the band of the standard recorded ECG. The standard recorded ECG band is −3 dB band with ranges from 0.1 Hz to 32 Hz.

A problem caused by noise is the overreaction of the recording system such that because of false repeat detections of the same sequence of arrhythmia, the memory overfills with segments of the same event. Such a problem is expected in Looping ECG recording systems which automatically detect an arrhythmia and then saves data that has been monitored for a period of time previous to the detection, as well as data from a period of time following the detection. We can remove some of this with our removal of noise, and some of this problem can be overcome by the use of redundancy in the trigger itself. (for example of redundancy, a string of 12 or 16 Tachy sized R to R intervals may be required).

A third source would be from electrical interference from other electrical devices in the area (EMI noise). Commonly this is in the 60 Hz range because most alternating current and devices run on this frequency. Any commonly available filtering techniques and digital signal processing techniques may be employed beyond what is described here for reducing this particular kind of noise.

A fourth cause of false detects may come from wide QRS complexes. These could include an inappropriate Tachyarrhythmia detection for the occurrence of a very long QRS segment caused perhaps by a patient with congestive heart failure if, for example, the tachy automatic trigger was short enough to register within a long QRS and the presence of high amplitude signals with noise caused multiple detections within that long QRS. (Thus, where the R-wave detector finds several putative R-wave detections during a single wide QRS, and the next QRS which also has several possible R-wave detections in it, a very short string of such events will cause a tachyarrhythmia event trigger to fire).

BRIEF DESCRIPTION OF THE DRAWINGS

FIGS. 1 and 2 are the exterior side view, interior block diagram, respectively of a prior art device.

SUMMARY OF THE INVENTION

Figure 3:
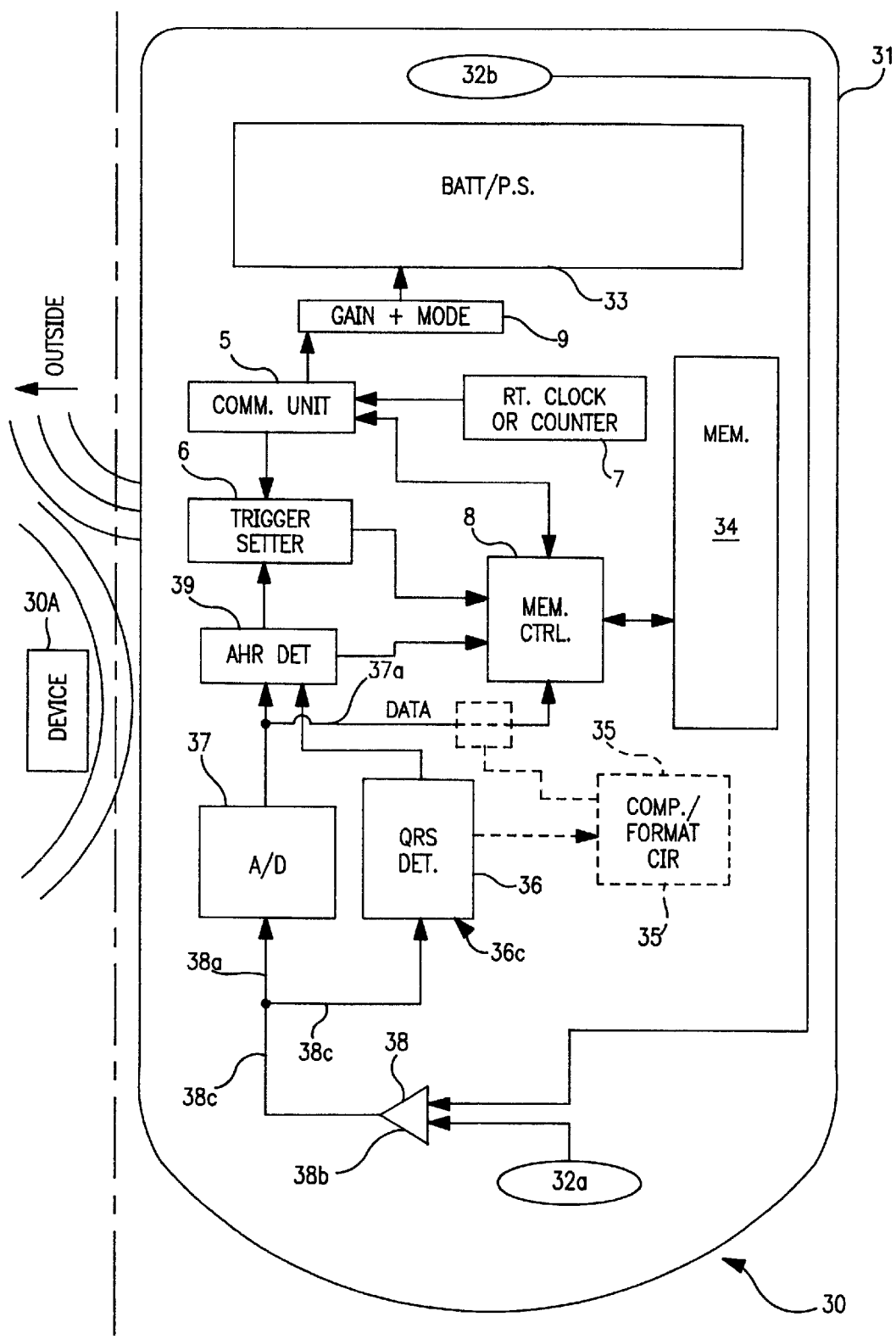
FIG. 3 is a block diagram illustrating the main circuit and assembly of a device in accord with a preferred embodiment.

This invention provides for the reduction in erroneous autotrigger activation of electrogram storage in an implantable medical device, and is particularly useful in devices with leads in the far field, that is away from the heart.

To accomplish some or all of the objectives inherent in the capturing of good ECG signals in the far field, we provide a method and apparatus which monitors for apparent R-waves and selectively discards consideration of some of them based on their occurrence within particular time periods. It may cause resetting of the automatic trigger's count in some circumstances.

This can be accomplished with particularized circuits for the required functions or by microprocessor control of system components as may be desired and as is described.

In general a denial period is started at the detection of an apparent R-wave and any senses next occurring within said denial period (which may also be apparent R-waves) are preferably ignored. An accommodation period starts either contemporaneously with or after the denial period. Apparent R-waves senses during the accommodation preferably extend the accommodation period. Preferably too, the accommodation period has an upper length limit so as not to infringe on the usefulness of bradycardia (Brady) or asystole autotriggers. It is possible to gain some noise reduction benefit without an accommodation period or without a denial period, or without an extension to the accommodation period, but it is believed to be most efficacious to employ all these innovations.

A single or multiple timers may be used. Variations on the autotrigger mechanisms (including Tachyarrhythmia (Tachy) or triggers set due to other sensor data used alone or in combination with R-wave sensing) may be employed and are expected in various preferred embodiments. Manually or patient activated and automatic triggers can be used contemporaneously with the autotriggers if desired, as well.

DETAILED DESCRIPTION OF THE PREFERRED EMBODIMENT

Prior to Medtronic Reveal™ implantable ECG monitor, the only consistent use of implantable electrode sensing systems employed leads located in the heart because of the quality of the signal obtained that way. Subcutaneous electrodes (below the skin, producing a far field electrocardiogram as compared to the intracardiac ECG available through most implantable devices today) have thus only recently been demonstrated to be effective in producing good monitoring devices, and have not yet found large scale commercial medical success. A well known example of a system having leads which also contained more than a single electrical contact in the body of the pacemaker was described in U.S. Pat. No. 5,331,966 issued to Bennett et al. in 1994, and incorporated herein by this reference. In column 8 of that patent, several other implantable recording systems are described.

An early implantable device is described with reference to FIG. 1 and which appeared at a NASPE (North American Society of Pacing and Electrophysiology) conference as a poster presentation in 1994. The device 10 was provided with two suture holes 13 and two spaced apart non-lead or leadless electrodes 12 at one and one-quarter inches distance center to center. The device was coated with paralene indicated by arrow 11 so that the only area of exposure on the body of the pacer can 19 is the exposed area at the electrode 12a. The other electrode is a metal plug electrode 12b mounted in a connector block 19.

In FIG. 2 the same electrodes 12 supplied signals into the circuitry inside the housing or "can" 18 (FIG. 1) by first entering a analog to digital conversion and amplifier circuit 14. Data from this circuit 14 was fed to a microcontroller 15 which provided functions of data compression, telemetry control and event capture triggered by patient operation. Telemetry block 16 and RAM memory storage 17 were also provided in this device.

Refer now to FIG. 3 in which a circuit block model 30 is illustrated in an outline of an implantable device which can be used with this invention, having a shell 31. Electrodes 32a and 32b bring signal from the body to an input mechanism 38, here drawn as a differential amplifier for simplicity only, the output of which is fed to a QRS detector 36 and an A/D converter 37. Both these circuits 36 and 37 supply output to an arrhythmia detector 39, which in this preferred embodiment supplies the autotrigger signal to the trigger setting circuit 6. The data output from the Analog to Digital converter may be converted, compressed, formatted and marked or reformulated if desired in a circuit 35 before the data is ready for input into the memory 34. The memory control circuits 8 receives input from the A/D converter, with or without conversion and so forth from circuit 35, from the auto triggering determination circuit (here seen as the arrhythmia detection circuit) 39 (which may include input directly from the QRS detector if desired) as well as signals from the trigger setter circuit 6. The trigger setter circuit may also be controlled by a communications unit 5 which operates to receive and decode signals from outside of the implant 30 that are telemetered or otherwise communicated in by a user. This communications unit 5 will also be able to communicate with the memory controller to request the off-loading of memory data for analysis by an outside device. It should contain an antenna or other transceiver device or circuitry to communicate with an outside device such as device 30A. A clock or counter circuit 7 reports the time since start, or real time, to the outside interrogator device 30A contemporaneously with a data off-loading session so that the events recorded in memory 34 may be temporally pinpointed.

Alternatives to this overall design may be considered, for example by using a microprocessor to accomplish some or all of the functions of circuits 6,8, 39, and 35 but it is believed that such a design will not provide the power and size savings taught by use of the preferred design. See FIG. 4 and accompanying description below for a microprocessor driven version.

Figure 4:
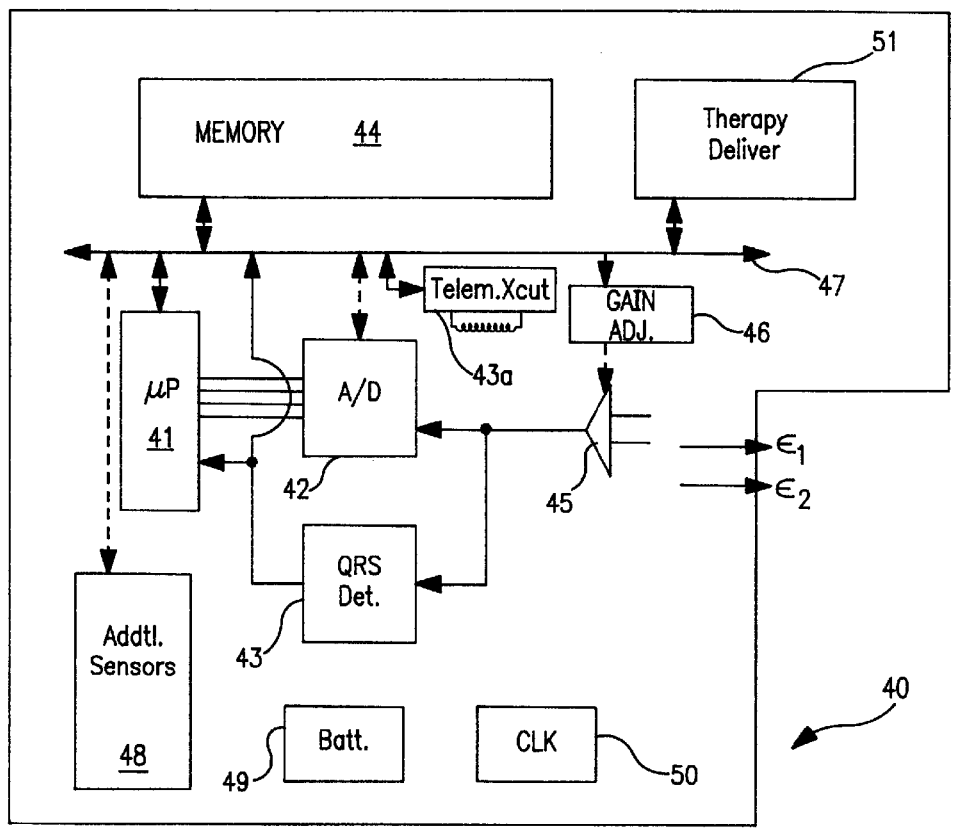
FIG. 4 is a block circuit diagram of an alternative embodiment to that illustrated in FIG. 3.
Figure 4A:
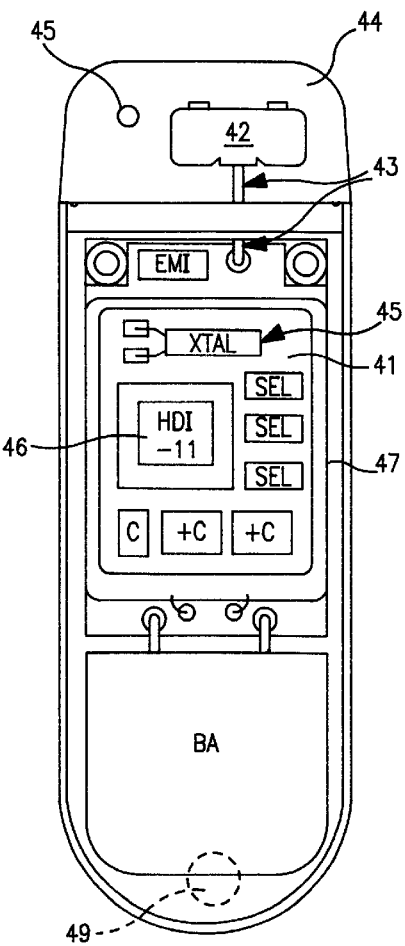
FIGS. 4A–4C illustrate the construction of the preferred form of the embodiment of FIG. 4.
Figure 4B:
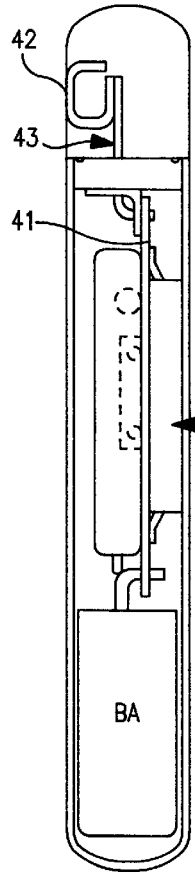
Figure 4C:
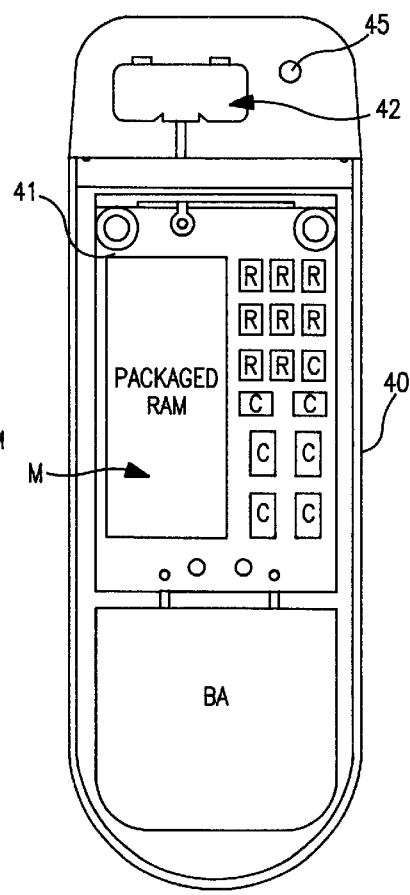

FIGS. 4A–C illustrate one preferred form 4 of the invention. In this form it has an outer titanium shell 40, in a plastic cap means 44, which together form the exterior of the device. The cap means 44 may be composed of material similar to those used for pacemaker connector blocks as it is in the is case. The two electrodes, 44 and 49, provide metal surface contacts to the body. Electrode 49 is formed as a whole in a paralene coating over the metal body 40, of the device. The metal electrode 42 is connected via a feedthrough 43 which is itself electrically connected to the circuit board 41. Circuit board 41 contains all the electronics required for the device function and is connected to a battery BA for power. An integrated circuit 46 houses circuitry and intelligence required for the function and the memory M is packaged on the other side of the circuit board. In this preferred form, the invention uses a communications circuit 45 having a telemetry antenna both to indicate from outside the body that a read out is requested of the device, and for communicating data out from said device. Programming of the device or mode setting will also use the communications circuit 45. In this form also a suture hole 45 is provided through the cap means 44. Electrode 49 is connected by a conductive connection (not shown in this fig.) to the circuit board. In this embodiment the length "1" is 2⅜" and "w" is ¾". These measurements can be varied within the constraints described. Electrode spacing here is about 1¾", center to center.

The exact sites of implant may advantageously be varied from patient to patient for various reasons apparent to the physician. Implant just under the skin now appears to provide the signal most free of skeletal muscle myopotential or body movement signal interference.

Referring again to FIG. 3, the external device 30A is preferably a device that is commonly called a "programmer" in the pacemaker art, because its usual function is to communicate with and program implanted devices. Software modifications and modifications to the telemetry system of device 30A to accommodate communication with and analysis of data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for mere ECG monitoring and event triggering is minimal, so in the preferred embodiments that only monitor some form of ECG or other limited sensory input, a microprocessor can be and is done away with altogether by using particularized functional circuits instead of doing the functions in software.

In FIG. 4, an alternative form of the implantable monitoring device 40 is illustrated, receiving input from two electrodes $E_1$ $E_2$ into an input amplifier 45. The output of the input amplifiers analog to digital converted in A/D circuit 42 providing an input data stream to the microprocessor 41. Additionally, a QRS detection circuit 43 monitors the analog output of amplifiers circuit 45 providing an output signal to either the micro processor 41 or the bus 47 as desired. In this simplified device 40 in this schematic of FIG. 4, the bus 47 will provide a data conduit for enabling and disabling functions of all circuits to which may be attached and for the transmission of data between the various circuits components and elements of the device 40. A telemetry transceiver 43 and memory circuit 44 will be able to move large amounts of data in a convenient way along this data conduit bus 47 as required for the operation of the system. Additional sensor circuits 48 may also provide data to the various circuits through the bus 47. A battery should be provided or other power circuit 49, and a clock circuit 50 would also be necessary to coordinate the transmission of data between the various circuit components and time their functions. Additionally, if desired, a therapy delivery circuit 51 may provide additional functions for the implanted medical monitoring device so that the device may take advantage of the data being gathered to deliver a particular therapy of use to the patient in a timely manner.

It believed to be most convenient to describe how the data is produced from the input signal with respect to the most preferred embodiment. However, it is also believed to be within the ambit of this invention to modify the following circuits for use with alternative embodiments such as the ones that may rely on a micro processor controller circuit as in FIG. 4.

Figure 3A:
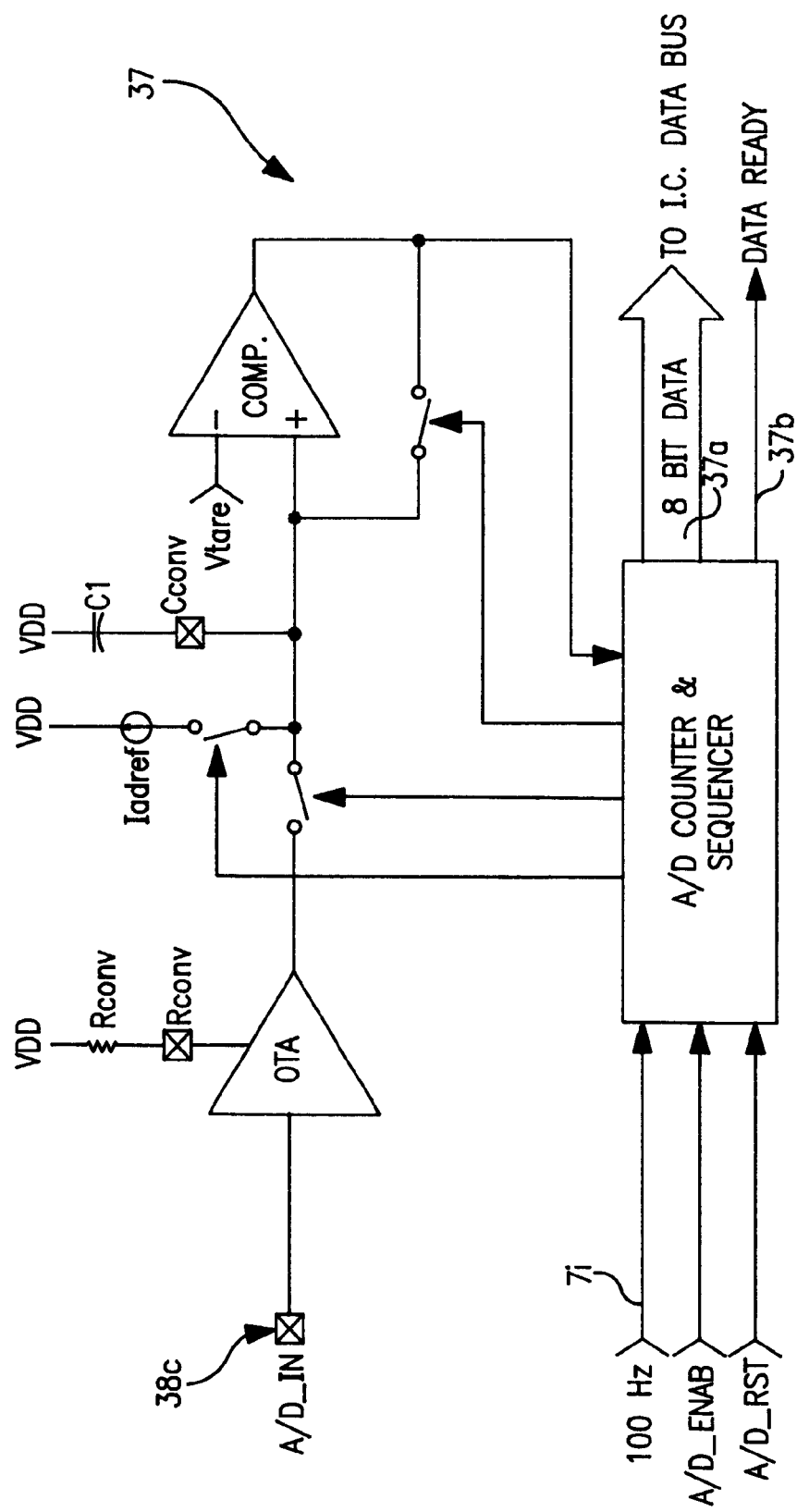
FIGS. 3A–D are block diagrams of preferred embodiment circuits of the implanted device used for monitoring and storing ECG's.

In FIG. 3A, a block diagram of an analog to digital conversion circuit for use in this invention is shown. The clock input may advantageously use an output from the clock circuit 7, input 7i. The input 38c is the analog input signal from input circuit 38, and the converted output is a stream of 8 bit digital data words on line 37a, sequenced by a timing line 37b.

Figure 3B:
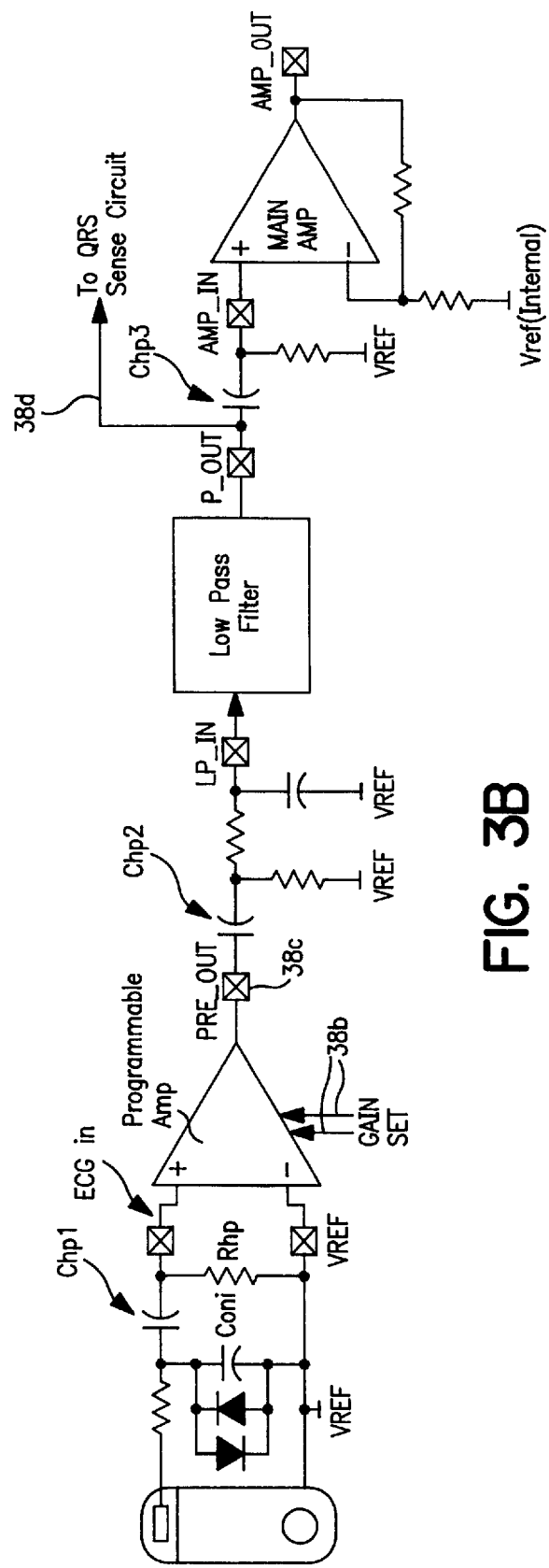

FIG. 3B illustrates the basic parts of circuit 38, additionally indicating the input of two gain set bits which can modify the value of the output of the low noise bipolar amplifier for output at line 38c, which after filtering will provide the input to the QRS detector at 38d. In this invention QRS detection is done on the analog signal, advantageously avoiding more complex detection required after digital conversion for the triggering of event storage.

Figure 3C:
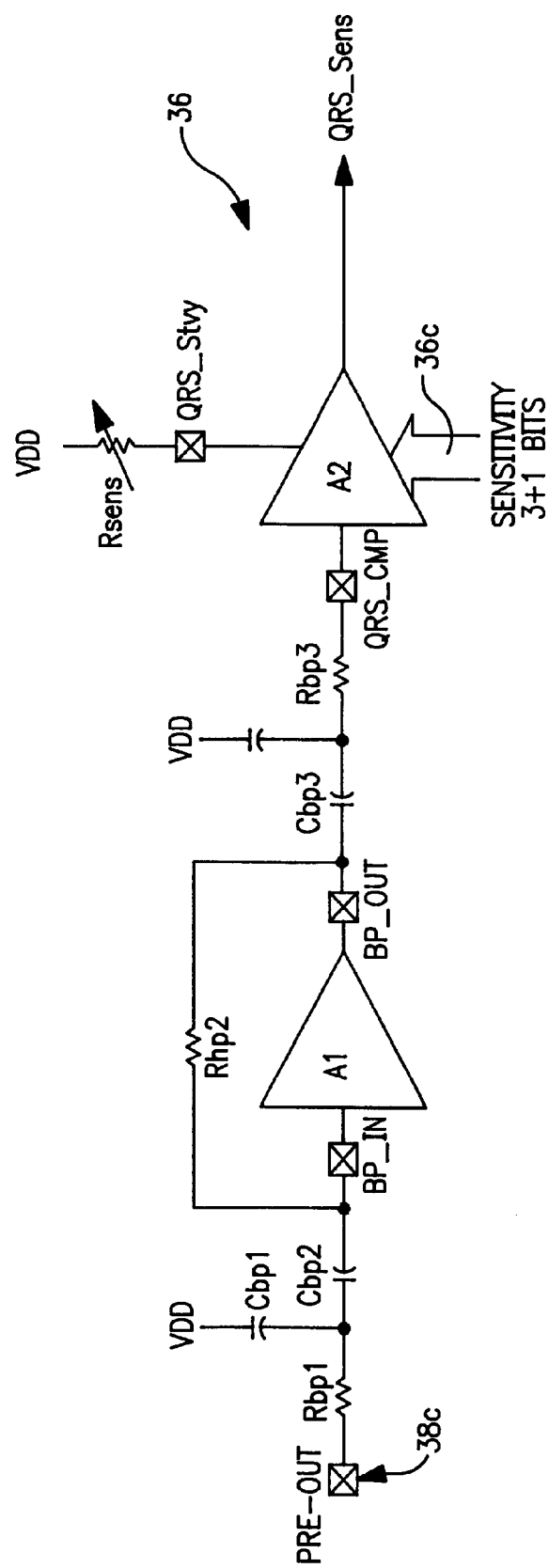

In FIG. 3C, QRS detect circuit 36 has a 2nd order bandpass filter with a center frequency preferably in the 20–25 Hz range. It includes a transconductance amp A1, summing amp/comparitor A2 and resistors Rbp1-3, capacitors Cbp1-4 and selectable resistor R sense connected as shown. R sense is preferably adjusted during manufacture. Additional control is provided for QRS sensitivity at line 36c, since the gain is detectable for this input.

Figure 3D:
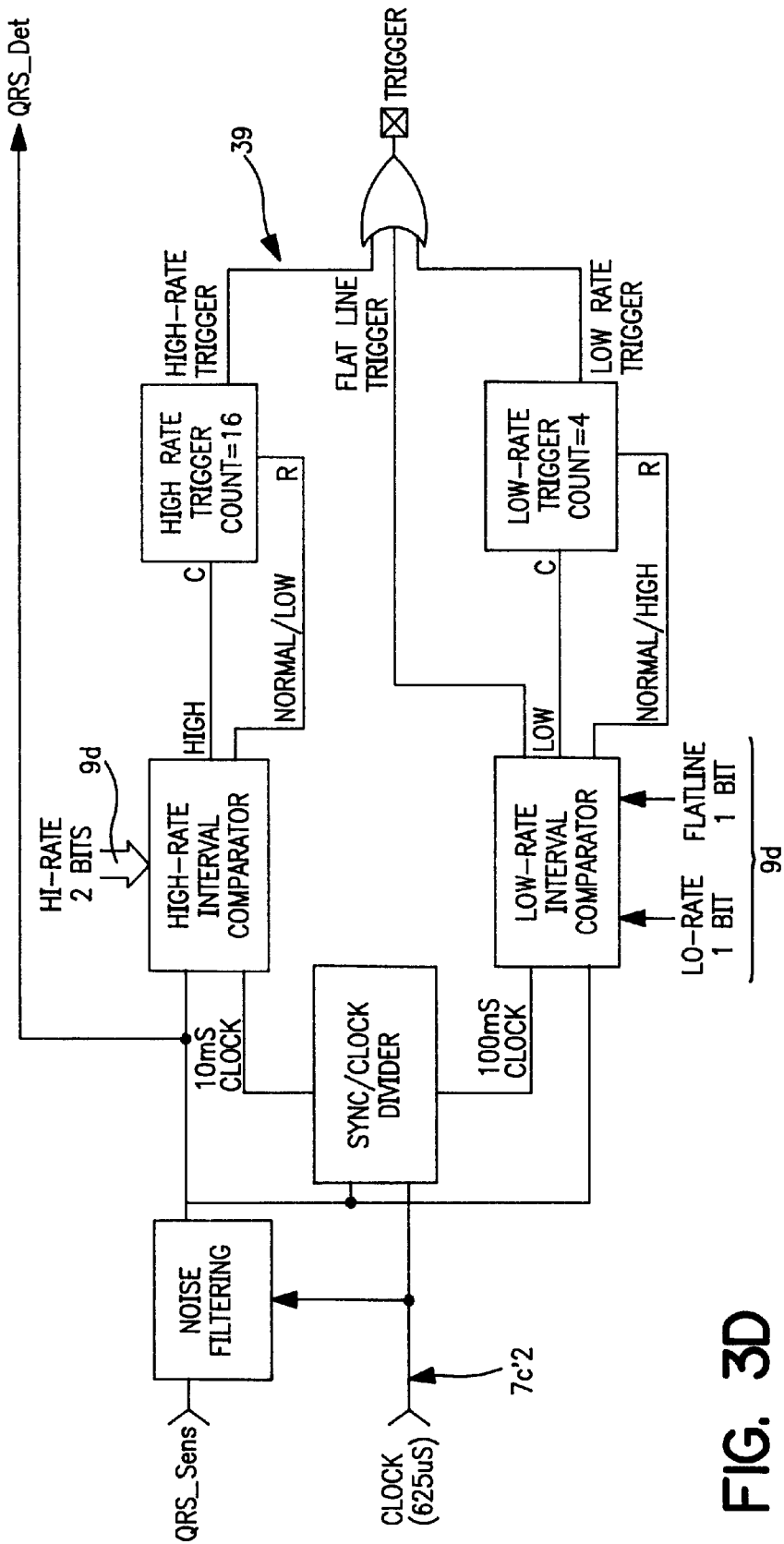

A simple arrhythmia detection circuit 39 is included with this preferred embodiment, and illustrated in FIG. 3D. The output from circuit 36 is monitored at a filtering circuit which provides in our preferred embodiment a denial period of about 85 mS and an accommodation period of about 180 mS, with some variation as described within. Timing is controlled by a clock input 7c'2. In the preferred embodiment, a high rate can be selected amongst four possible high rate values in our preferred embodiment, with two selection bits dedicated to do so at input 9d and the low and flat-line trigger rates each have one bit to turn them on or off provided by inputs 9d. These inputs designated 9d preferably come from a register that holds the gain the mode and the rate settings, illustrated as register 9 in FIG. 3. Such features may be programmable through communication with the implanted device by an external device. One example of a preferred timing for the high rate (also called Tachy) triggers is 140, 162 and 182 beats per minute, but we can have seven or more settings in some preferred embodiments, and each requires 8 to 32, preferably around 16 or more, consecutive beats at such a rate to initiate the trigger. Our most current embodiment provides a rate flexibility for the trigger value of seven different tachy trigger rates. Additionally the trigger may be programmed off, i.e., inactive. The low rate counter/comparitor may be programmable to detect low rates of 40 or 30 bpm, requiring 4 consecutive low rate intervals to trigger. Additionally a flat-line trigger can be set to occur after 3 or 4 and one half seconds of no QRS detection.

Clearly, the noise rejection taught here is primarily to enable the functioning of the triggers in the presence of noise. However, where the nature of the ECG signal or the interaction of it with the auto triggers might cause the auto-triggers to miss out on valid R-wave signals, an additional sensor (or more than one) may be provided to trigger the capture in memory of the ECG signal at such times, with a value from the additional sensor, or not, as may be preferable. Thus, if a wide QRS is causing the continuous extension of an accommodation period, a contemporaneous sensor signal showing poor oxygenation or poor blood pressure or other indicator of poor cardiac performance could, if the indication is strong enough trigger the ECG storage. Falling down from fainting could be picked up by an accelerometer which would also be a useful trigger. Too, if one of the R-wave based triggers set off the activation or triggering of an ECG record. (For example, a series of wide QRS segments may cause oversensing of apparent R-waves to set off a tachy trigger as would a series of inopportunely timed EMI pulses). It would be advantageous to record at the same time that such a trigger is set off or should be set off, the level of measurement made by the physiologic sensor(s) which may also be present in the implantable device. This would enable the physician or researcher to tune the noise filtering to better enable useful automatic triggers to the patient, or eventually allow for automatic tuning of auto triggers, based on physiologic measurements made at the time an ECG record is made. For an example of this, by knowing the kinds of signals being missed, say a wide QRS, due to too many extensions of the accommodation period, the operator of controls on the device can tune down the length of either the first accommodation period, the length of extensions, the existence of extensions or even the denial period length, as may be most appropriate for the particular conditions, due to physiologic or extraneous noise, present in a particular patient. Therefore, for embodiments that include more sensors and/or electronics, an additional sensor could be added to benefit the patient.

If other sensors are used, their output could be stored with the ECG memory data for enhancing the information available for diagnosis and treatment.

One particularly useful would be an activity sensor based on a single or multi-axis accelerometer, which indicates the level of patient activity and his orientation. By checking for output that indicates the occurrence of a VVS (VasoVagal Syncope) episode, (for example, the patient falling from an episode) such an addition offers an improved trigger for events that might otherwise be missed by an arrhythmia detector set up like in FIG. 3D. Such a sensor trigger could replace the circuitry of 3D.

Additional circuits may be provided to support additional functions if desired, however in order to reduce size and power consumption and extend the life of the device and reduce the intrusion into the body of the wearer, auxiliary circuits should be kept to a minimum. Such additional circuits could support oxygen sensing, pressure sensing, respiration sensing, and any other kind of sensing that can be demonstrated to have been known for implanted devices. They may each have their own auto triggers based on sensor output, or depend on manual triggers. Additionally, activity sensing or positional sensing devices can provide additional input for recordation and or autotriggering functions. As new sensors become available they may also be incorporated into these designs.

In considering size, the maximum dimension of the device need be only the minimum required dimension for good signal to be obtained from the two electrode areas. In our studies we have found useable signal for ECG monitoring at a distance of about ½ inch (1 cm). The best minimum electrode distance for current electronics at reasonable prices appears to be from ¾ inches to 2 inches. Of course if the inventive features described herein are incorporated into a pacemaker or ICD, one could so, employing therapy delivering features of such devices in conjunction with the data recording features of this invention.

Limiting Noise in Accord with Present Invention.

Figure 5:
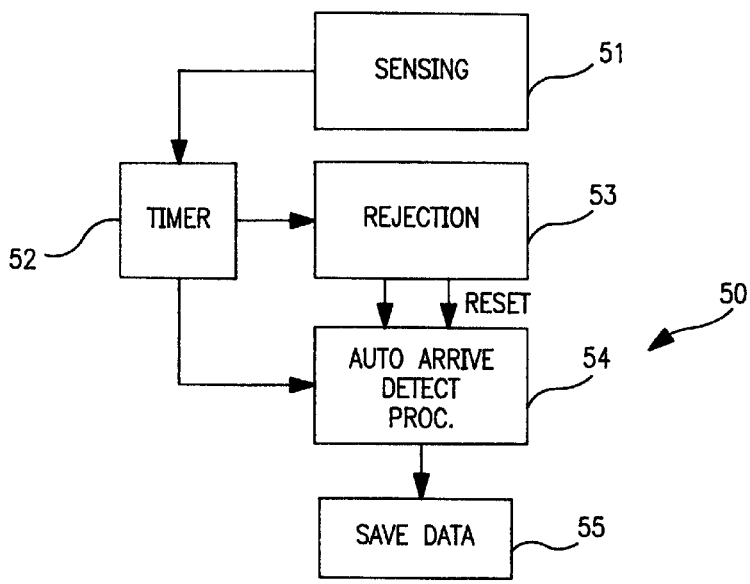
FIG. 5 is a heuristic block diagram of processes for use by the invention.

There are essentially five processes which occur more or less simultaneously in order to accomplish the requirements of this invention. In FIG. 5, the five processes are shown in a block diagram 50. The device for recording ECG's must have a process for sensing 51 when R-waves occur (other indicia of the need to record data ) and a process for rejecting senses of apparent R-waves in block 53. A process timer or a group of timers in block 52 is responsive to the sensing of at least one R-wave from process 51 and the rejection process 53 is dependent upon the timer process 52. The automatic arrhythmia detection process 54 is also dependent upon the timer process and can be reset in part or in whole by the rejection process 53. When a proper indication of a arrhythmia is detected in process 54 an additional process 55 of saving the appropriate data, preferably an ECG segment surrounding the time period in which the automatic arrhythmia detection process sets off a trigger.

Figure 5A:
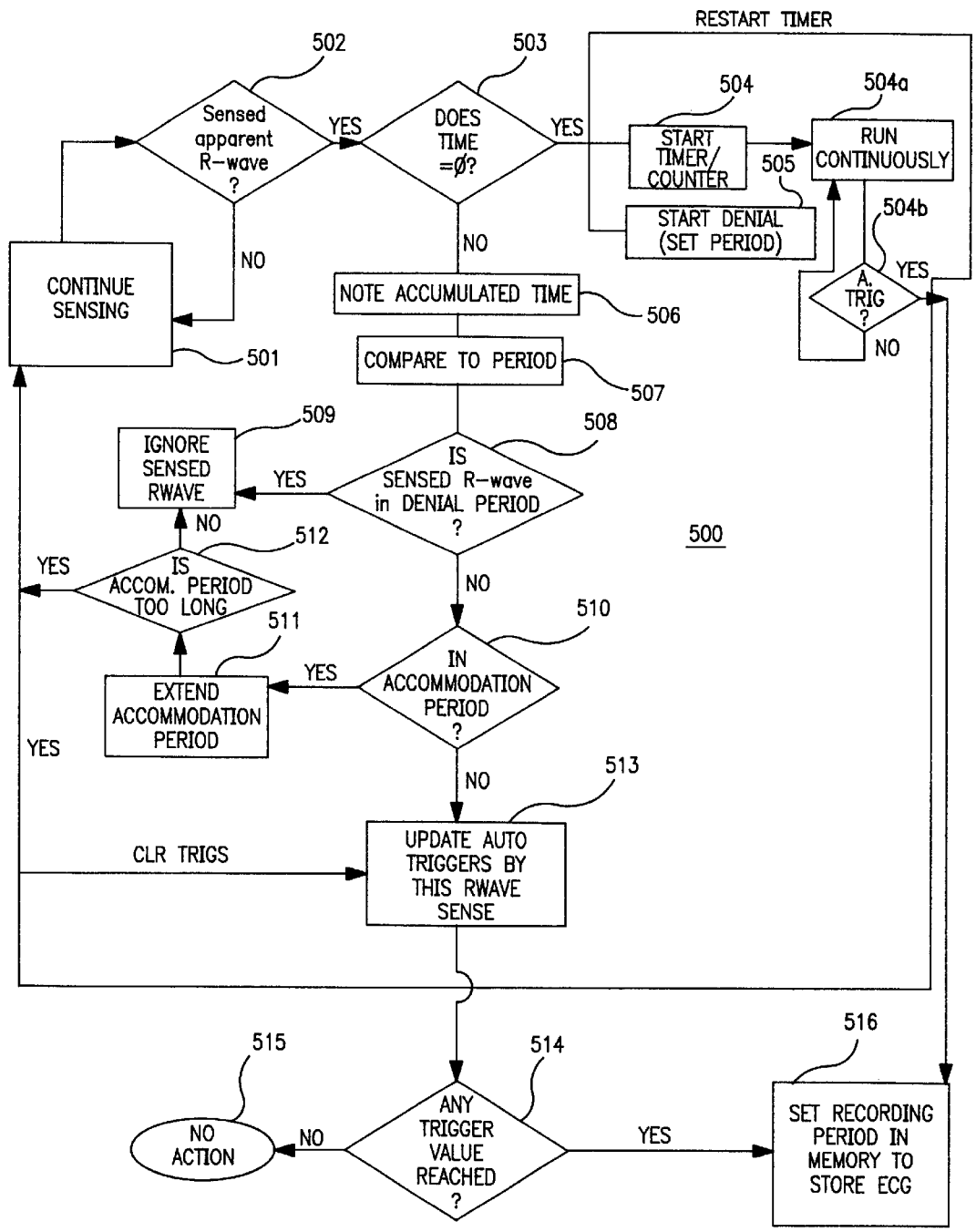
FIG. 5A is a flow chart of a preferred embodiment process flow arrangement.

Please refer now to FIG. 5A. Here the process flow diagram 500 illustrates the features of the five processes of FIG. 5.

In the preferred embodiment, the device will always be sensing R-waves here illustrated as step 501. Based on whatever criteria, the answer to the question in step 502 can be yes. In our preferred embodiment a adequate change in the amplitude of the output of the R-wave sense amplifier maybe used for producing a signal indicating that an R-wave has apparently been sensed.

In our preferred embodiment we accomplish all the timing processes with a single timer (or counter) although multiple timers can be used. If after an R-wave one of the timers that must be working is set to zero (step 503), the timer or counter must be started step 504. Also, if the timer was at zero and we have detected a R-wave or sensed a R-wave and are starting the timer in step 504, then we should also start the denial period in step 505. (This can be done by setting a latch that goes off when the timer or counter reaches the length of the denial period which in the preferred embodiment is 65 mS but can vary several milliseconds around that time in length. Also, after the timer is restarted we are again sensing either after the denial period expires or immediately. After a next apparent R-wave is sensed and the timer is no longer at zero as determined in step 503 the accumulated count of time will be noted in step 506 and compared to the various trigger periods in step 507. It must be determined in step 508 if the sensed R-wave is in the denial period. If it is in the denial period than we ignore the sensed R-wave in step 509 and continue sensing by step 501. There are several ways of course to do this including, turning off the continues sensing during the denial period and turning it on again when the denial period is over. But for the purposes of simplicity here in the preferred embodiment we continue as illustrated in this FIG. 5A.

If the sensed R-wave was not in the denial period in step 508 than the next determination must be made. Was the sense occurring in an accommodation period (step 510)? If it was in the accommodation period than an extension to the accommodation period must be made in step 511. If the accommodation and the extension period are too long the determination made in step 512 will produce several reactions. In the preferred embodiment sensing is continued and the appropriate triggers (Asystole) will be cleared back to zero. The timer will also be restarted.

If however, the next apparent sensed R-wave is outside this accommodation period the sensed R-wave will be counted as against the ongoing autotrigger counts in step 513. In step 514 an evaluation of these autotrigger counts will be made and if no trigger value is reached than no action will be taken 515. If a trigger value is reached, the trigger activates the storage of an ECG segment in the memory step 516.

Because one of the triggers in the preferred embodiment is an asystole trigger, once the timer is started, the asystole trigger timing runs continuously in step 504A, and if no apparent sensed R-wave is detected within an appropriate time for the asystole trigger to be triggered in step 504B, then the timer will be restarted and, step 516, the recording of a ECG segment will also be initiated. In a less preferred embodiment, an insufficient number of R-waves senses found within a certain length of time may initiate a Brady trigger also, however, we prefer to insure that there are a sufficient number of beats at a bradycardia interval/rate so our preferred rate of bradycardia trigger will be different. (Four beats at a designated "Brady" rate).

Figure 6:
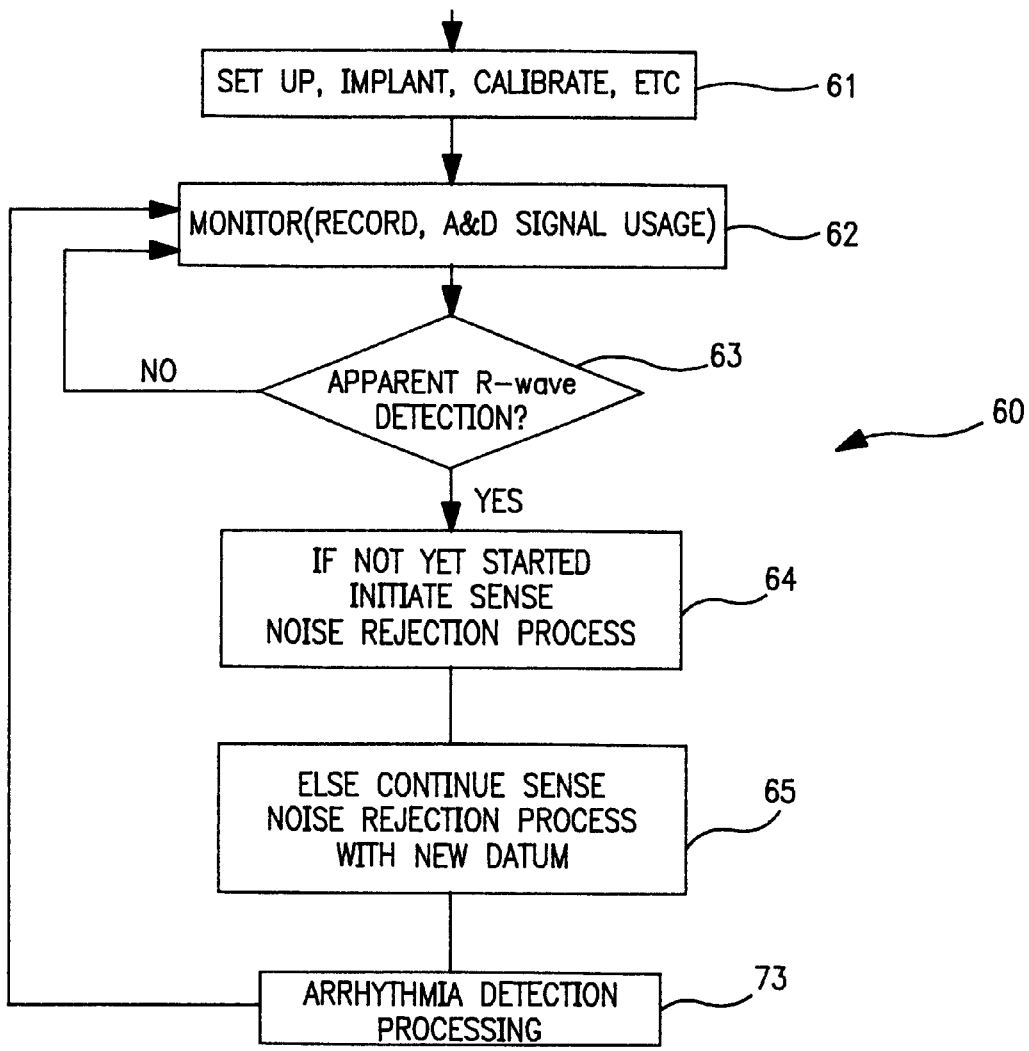
FIG. 6 is a flow diagram illustrating a preferred embodiment.

Refer now to FIG. 6 in which an alternate description of the process for eliminating significant amounts of noise from the electrocardiogram signal which will be employed for triggering activation of data storage is described in flow diagram 60. It is usually necessary to set up, implant, and calibrate the implantable medical device and this is encompassed in step 61. To begin, the implantable medical device will monitor the electrocardiogram signals in step 62. In this step 62, which is described elsewhere in more detail, the implantable medical device will be continually monitoring the electrocardiogram signal from an input amplifier and recording (into the memory) segments of the signal that have been analog to digital converted. The device preferably will also be monitoring the analog signals for features which might indicate the presence the R-wave in the electrocardiogram. (There are numerous methods known to detect QRS complexes or also called R-Waves in the electrocardiogram signal. Because this is so well-known in the art an exact description of a preferred detection scheme would be unnecessarily limiting. A simple yet useful detection scheme would be to monitor a deviation in amplitude of a certain percentage or amount over an appropriate period of time, for one example. Even simpler might be when the amplitude punctures a certain level or envelope. Any known method and apparatus for detecting R-waves can be used). When a sufficient electrocardiogram feature is sensed, indicating an R-wave is detected (which we call R-wave sensing), the query in step 63 (does it appear that an R-Wave has been detected?) can be answered positively and we can then determine how to proceed further. If the process of noise removal has not yet been started at the time of a first R-wave sensing, in step 64, the inventive noise removal process should be initiated. Otherwise, in step 65 the process should be continued with the new data of the apparent R-wave sensing from step 63. At this point the process will return to the monitoring phase of step 62. While this step 65 process is occurring, the monitoring for arrhythmias also occurs, here indicated at step 73.

Figure 7:
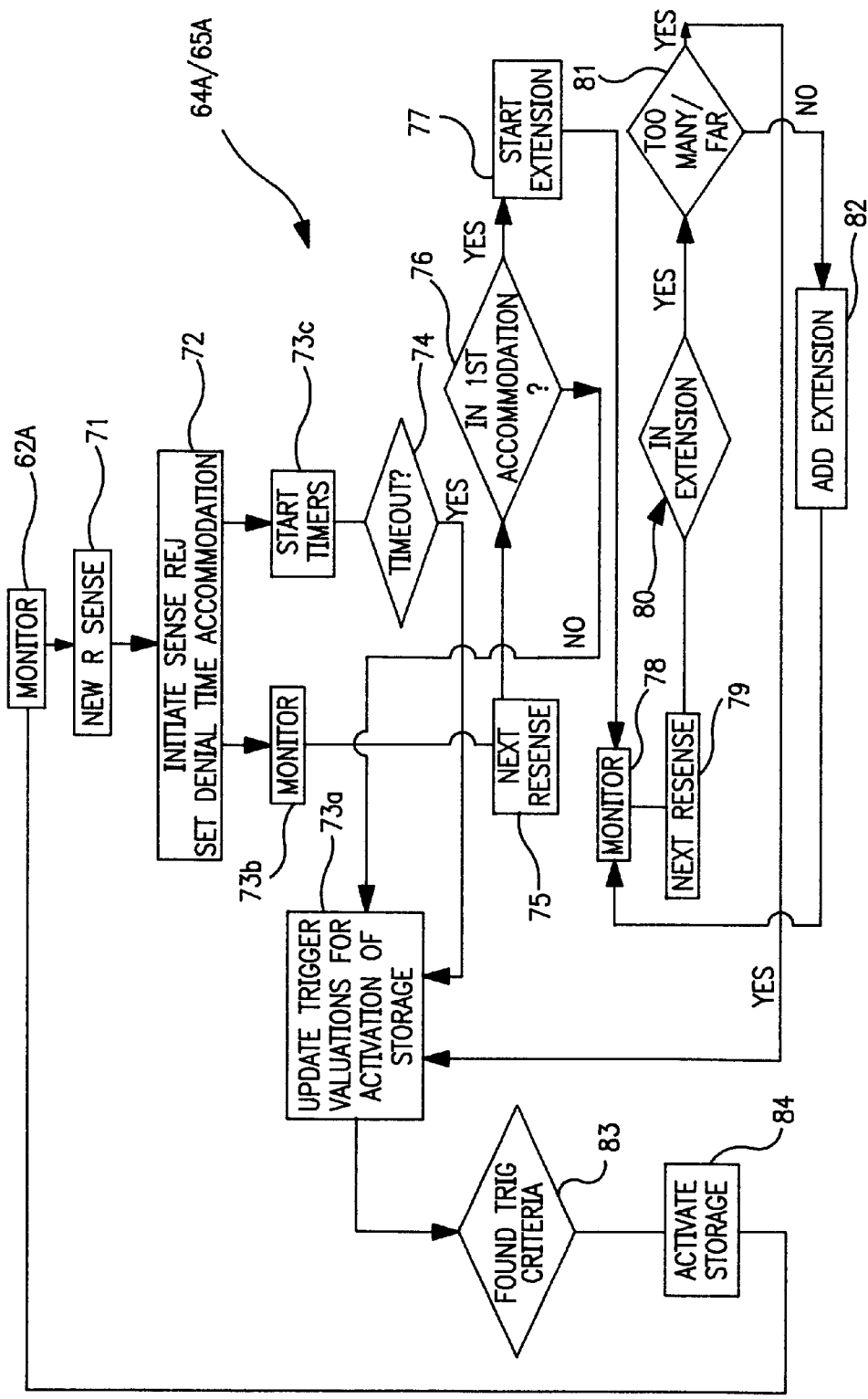
FIG. 7 is a flow diagram detailing other aspects of the preferred embodiments.

Referring now to FIG. 7, the noise rejection processes of 64 and 65 in FIG. 6 are explained in the flow chart 64A/65A. From the monitoring step 62A, a new R-sense may be sensed in step 71. This will first initiate the noise sensing rejection process, setting a denial time period and a first accommodation period in step 72. If another R-wave is sensed during the denial time period, the R-wave will be ignored completely for the purposes of noise rejection. This is because the heart itself should be in a refractory period for a short period of time surrounding the R-wave in the electrocardiogram. Furthermore, especially in patients with congestive heart failure, a very long R-wave may cause a double sensing of apparent R-waves during some of the very wide R-waves that congestive heart failure patients may have. In general too, any kind of noise that might find its way into the ECG signal at this time is unlikely to be physiologic in nature and can thus be rejected. If there are no arrhythmia detection triggers pending (a discussion of what triggers are is within the description of FIG. 7) then there is no need to update the trigger evaluations in step 73a but we will need to start timers in step 73c to initiate trigger evaluations and continue to monitor for new apparent R-wave senses in step 73b, step 72 also specifies the end of denial time or starts a counter/timer for it setup in step 72. The other thing that is setup in step 72 is the first accommodation period. When a time-out of one of the timers initiated in step 73c occurs, the process moves on to step 73a. The first time-out considered is the time out of the first accommodation period.

Figure 10:
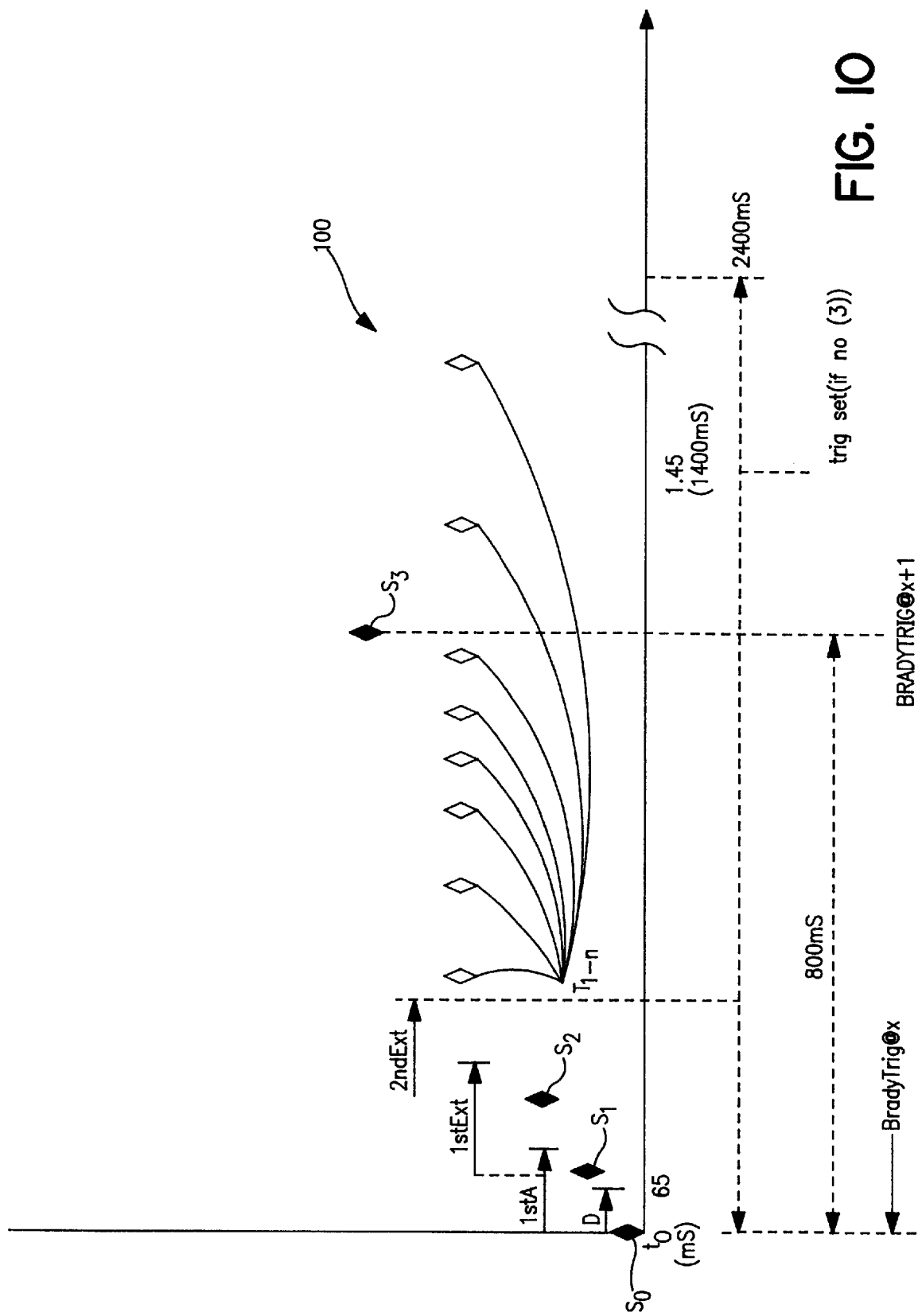
FIG. 10 is an alternative graph of some time periods for use with this invention.

Refer now to FIG. 10 in which a graph 100 illustrates the occurrence of the events within a preferred embodiment device, in sequence.

At time $t_0$ the first apparent sensed R-wave $S_0$ occurs. The denial period begins and runs for 65 mS as shown. Also the first accommodation period (1stA is set and runs, preferably from the beginning of the denial period). The second sense $S_2$ occurs within the first accommodation period. This causes the first extension, preferably of 150 mS to occur. Thus, the second sense $S_2$ occurring within the first extension of the accommodation period initiates a second extension period to run. No sense occurs within the second extension. Suddenly a Tachy arrhythmia episode occurs lasting for eight beats T1-n. This occurs during a 300 mS window outside any extension periods. Therefore if the Tachy arrhythmia detection criteria would set a tachy trigger to record a electrogram after the occurrence of sixteen beats within 2400 mS or sixteen tachy beats within 3200 mS or somewhere within that approximate range. Here the Tachy beats (the open diamonds T1-n) only add up to eight beats or nine counting the beat at $S_0$ within the 2400 mS and so the tachy trigger would not be set to record an electrogram. A Brady trigger on the other hand will be reset by the second beat at 800 mS ($S_3$ after beat So both of which are recognized because neither of which are within a denial or accommodation period or an extension to an accommodation period). Brady triggers should be set preferably within thirty to forty beats ranges and should not be activated until after a series of at least three and preferably four senses within such ranges.

Having described in overview how the trigger value evaluations are monitored, in step 73a, along with the timers of step 73c we can move on to the next step and for this we refer back to FIG. 7. When another R-wave is monitored, the noise detection process can be enhanced by extending the accommodation period. The first step in this process, step 76 checks to determine if we are in the very first accommodation period after a denial period. If the process is in the first accommodation period and the answer is yes, we can start the extension in step 77 and continue to monitor in step 78. At the next new apparent R-wave in step 79, if we are in the extension period of the accommodation period in step 80, we next need to check to see if the extensions have gone to far and are interfering with our Brady sense trigger detection criterion or our asystole trigger detection criterion. This would happen if the accommodation period has extended so far that the ability of the trigger to react is lost since the accommodation period has subsumed or compromised too much of the range of time the trigger needs to be timing out without finding an R-wave. If the extensions have not subsumed the trigger period, or a substantial portion of it, the process should add another extension in step 82 and go back to monitoring in step 70a. (This monitoring for new R-waves could be called an acceptance period, i.e., that time left after accommodation before a trigger is set off in which the monitoring of R-waves can be continued.) If the extensions are so long that the acceptance period is insufficient to provide time for a reliable trigger, then we need to update the trigger evaluations by restarting the timers for such triggers at zero.

Figure 8:
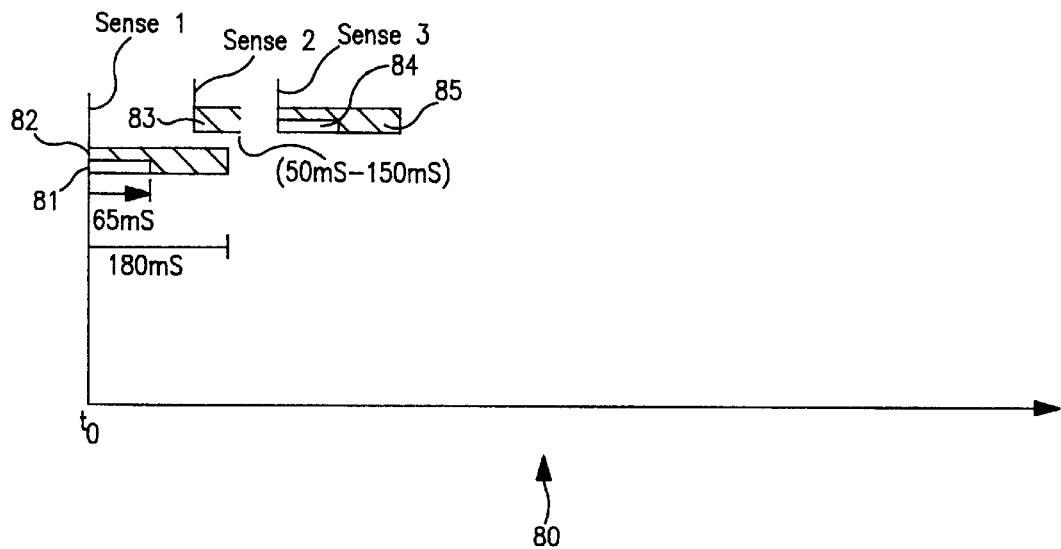
FIG. 8 is a graph of time and periods used in a preferred form of the invention.
Figure 9:
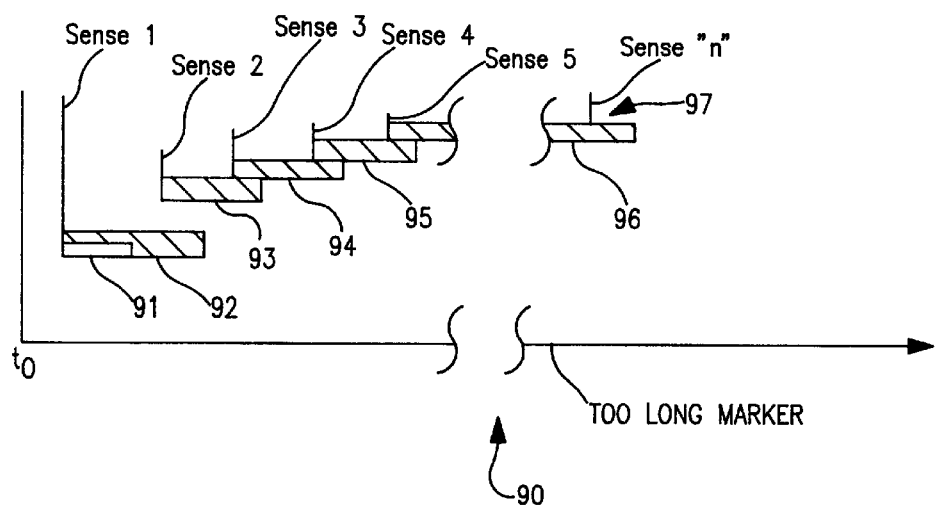
FIG. 9 is another graph of time and periods used in a preferred form of the invention.

Schematically, this process is illustrated with reference to FIGS. 8 and 9. The first sense at $t_0$ initiates a denial period 81 or 91. This is preferably 65 mS, although reasonable variation is fine. The first accommodation period is preferably around 80–200 mS, most preferably 180 mS, although other similar time periods can be chosen. Extensions for R-waves sensed within the first accommodation period can be anywhere on the order of from 50–150 mS, and may be variable by order or made in identical increments, as desired. (Thus they could all be 150 mS, or the first could be 150, the second 140, and so on until the maximum allowable extension is reached. If the second sense (sense 2) occurs within the first accommodation period (82 or 92), an extension is provided (83, or 93). If a third sense (sense 3) occurs within the accommodation period extension 93, a second extension 94 issues. For a fourth sense and a fifth sense and so on these extensions continue. If the extensions continue for too long however as illustrated at extension 96, and a new sense (sense n) will not produce an new accommodation extension here illustrated as the blank space at 97. Further, the trigger period will have timed out for systole at, for one example, 1400 mS, and that trigger should be reset.) Also, if preferred, the designer could have the extension period start at the new R-wave sense for a fixed period of time, or the extension could be started at the expiration of an accommodation period in which an R-wave is sensed. However, if the last extension for an accommodation period has expired (83) subsequent sense comes in (sense 3), a new denial period 84 will start and a new 1st accommodation period will be restarted as well.

ECG Recording Functionality for Preferred Embodiments.

The most important function of the simple versions of this invention is the long term electrocardiogram (ECG) monitoring of the subcutaneous (or intramuscular) ECG. The device continuously records and monitors the subcutaneous ECG in an endless loop of memory. In its primary mode the device is triggered to save/retain in memory the last few minutes or seconds of ECG data by the patient subsequent to feeling symptoms of interest (e.g. syncope, palpitations, etc.), plus some period of time prior to the trigger.

In the preferred embodiment with 128K of memory the device can store 42 or 21 minutes of ECG, which can be reset after off-loading by telemetry to an external device for analysis and display. In one form there are four modes settable for patient trigger only and in another form there are autotriggers. In the patient only (also called "manual") trigger modes, the patient can capture either one or three events between off-loadings at either no compression or at a compression ratio of 1:2 or some other device supported ratio. When setting the mode of the implant, the physician or attendant can decide whether to record data in a compressed mode or not in the preferred embodiment. If greater detail of the triggered ECG is required than can be developed from compressed data storage, the physician should select non-compressed recording, thereby limiting the time available to record. In some embodiments sample rate may be modified as well, but this is not preferred.

Compression is preferably done using a known compression algorithm implemented in hardware. Many types are known and software compression could be used if desired too. An excellent and easy to implement example is found in the article Arrhythmia Detection Program for an Ambulatory ECG Monitor by Mueller, copyright 1978, ISA, ISBN 876645. Using this algorithm in one embodiment we have used a pre-trigger time of record of a maximum of 2400 seconds and a maximum post trigger record of 120 seconds, and at the higher sampled or less compressed rate of 1200/60 for a single event and 360/60 seconds for three events. These time values are obviously only examples and the reader can set whatever time he or his physician feels is appropriate within the ambit of this invention. After such a record is made the device memory locations are full and will be overwritten by the next triggered event since in the preferred embodiment the memory is maintained in a continuous loop.

Additional modes include those with pure autotriggering, which can mirror the patient triggered only modes if desired. It should be considered that with autotriggered events, the determination by the device of an event worth recording and the subsequent activation of the trigger by the device itself will be faster than the patient finding his device for activation or otherwise activating the device, so the pre trigger time record can be smaller. In one preferred embodiment the memory is segmented to allow for 14 autotriggers and 3 manual triggers. Further detail regarding modes is described with reference to FIGS. 11 and 12.

The patient activated triggering of a preserved form of the recorded ECG signal can be carried out by using a small hand-held external device which may be of any number of different forms. A first way is through a hand-held battery-powered device which uses a coded radio-frequency telemetered signal through the skin to the device, on the press of a button. A simpler device a small hand-held used to close a magnetic switch within the implanted device to trigger it by holding the magnet close or patting the area of the body that has the implant a set number of times with the magnet. Other methods for triggering ECG data retention in memory (each of which has it's own advantages for implementation) are to use physical tapping or slapping of the finger or hand on the skin over the device in a particular cadence and/or number of taps (advantage is that no triggering device is needed. With such methods the disadvantage is that the patient needs to memorize the triggering sequence. Matched voice activation with a known command is possible but the complexity at this time of discerning voice commands precludes such activation for the present time, but could be in future devices using this invention. Another approach is light activation through the skin using a light source and receiver, auditory/sonic activation using a hand-held auditory/sonic source held over the skin with a microphone receiver in the device. All these methods are patient activated and require patient compliance or cooperation, a feature this device was designed to avoid. Accordingly in conjunction with one of these patient triggers or alone, an automatic activation or trigger for holding a chunk of memory should be included. This could be activated by automatic recognition of an arrhythmia, a heartbeat too fast or too slow, or for any other condition the device may be set up to find.

If a patient trigger is used it is advantageous provide feedback to the patient regarding whether the attempt to trigger long term storage of the event was successful. To accomplish this the implant should telemeter out a signal that indicates it has recognized a valid trigger. (This of course requires additional circuitry and usage of the limited available power supply.) The external triggering device then notifies the patient via the triggering device or through some known alarm mechanism whether they have or have not properly triggered the implanted device. This notification can be one of any combination of a number of feedback methods including: one or two visual sources such LED's, an auditory source such as a beeping speaker in one or two tones, or a tactile source such as a vibration. See also U.S. Pat. No. 5,518,001 (incorporated herein by this reference) for other potential trigger-indicator ideas for a hand-held patient activated trigger device.

Features and Construction of the Preferred Embodiment Implantable Devices.

Figure 11:
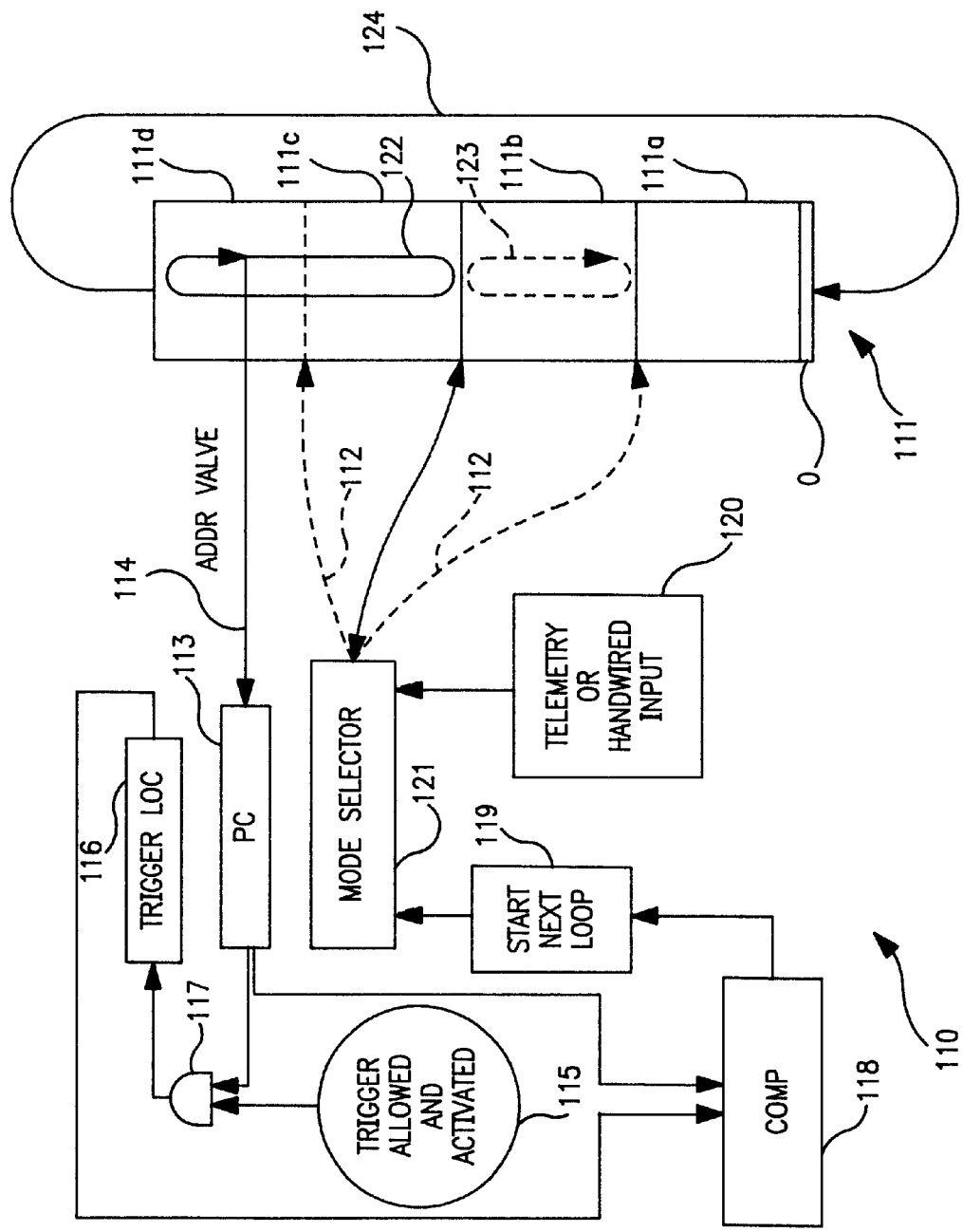
FIG. 11 is a block diagram of the looping memory and its control circuitry in accord with a preferred embodiment of the invention.

Referring now to FIG. 11 in which a block diagram of a functional model 110 of the controller and memory 111 of a preferred embodiment device is illustrated. The memory is generally organized as a continuous loop of, preferably, 8 bit addresses starting at address 0 and looping back around to address 0 through line 124. By telemetry or hard-wired input during manufacture 120, a mode selector 121 is set so as to divide the memory 111 into working segments 111a–d. The address of the start of each of these segments is indicated with lines 112.

Since this device is used for recording physiologic data, after the data is compressed, converted, formatted and is in appropriate digital form, it is continually recorded in the memory 111. The address value at the tip of arrow 122 in the combined memory space 111d, 111c is monitored by a program counter register 113.

The size of each memory segment set in a given mode limits the amount of data available for each triggered event. In the preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7, (the patent being incorporated herein by this reference in its entirety.

To use a single program counter the actual trigger address minus the time (in memory location storage events) required to have already stored the amount of data needed for pre event analysis for that trigger is stored as a value in the trigger location register 116 of FIG. 11. If a larger time for pre trigger recording is required by a trigger occurring during an already triggered event,(say, a manual trigger follows the occurrence of an auto trigger), the value in the trigger register can be decremented, thus yielding a larger pre trigger time period in the allocated memory segment for this event. A priority system for whether to extend the pre trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto triggered one because upon recovering from an event the patient has enough time to recover, get their wits about them, and find the triggering device. Manual triggering may therefore be set to record in double or multiple sized segments. FIG. 11's segments 111c and d are joined by looping arrow 122 to give effect to this concept.

Because the memory size is preferably quite limited a time record or first-in-first-out pool record should be kept on order that the newest triggers record only over the oldest events segments. An additional preferred feature allows for a mode that prevents recording over any triggered event segment. This is preferably implemented by a counter which fills for each segment used and has storage for the set number of looping segments. When it is full recording of new events stops.

When a trigger is activated and under the control program of the device is allowed, a signal 115 is permitted by some control gate 117 to allow the program counter address to be loaded into a trigger location address register 116. After loading, each subsequent clock cycle or set of clock cycles depending on the configuration of the device will load the trigger location from 116 into a comparator 118 to compare this location with the program counter address stored in register 113. When comparator 118 finds that they match, an appropriate output is generated to start the next loop via control circuit 119. This control circuit 119 will cause the mode selector to point to the next available loop location effectively placing that into the program counter 113.

Figure 12:
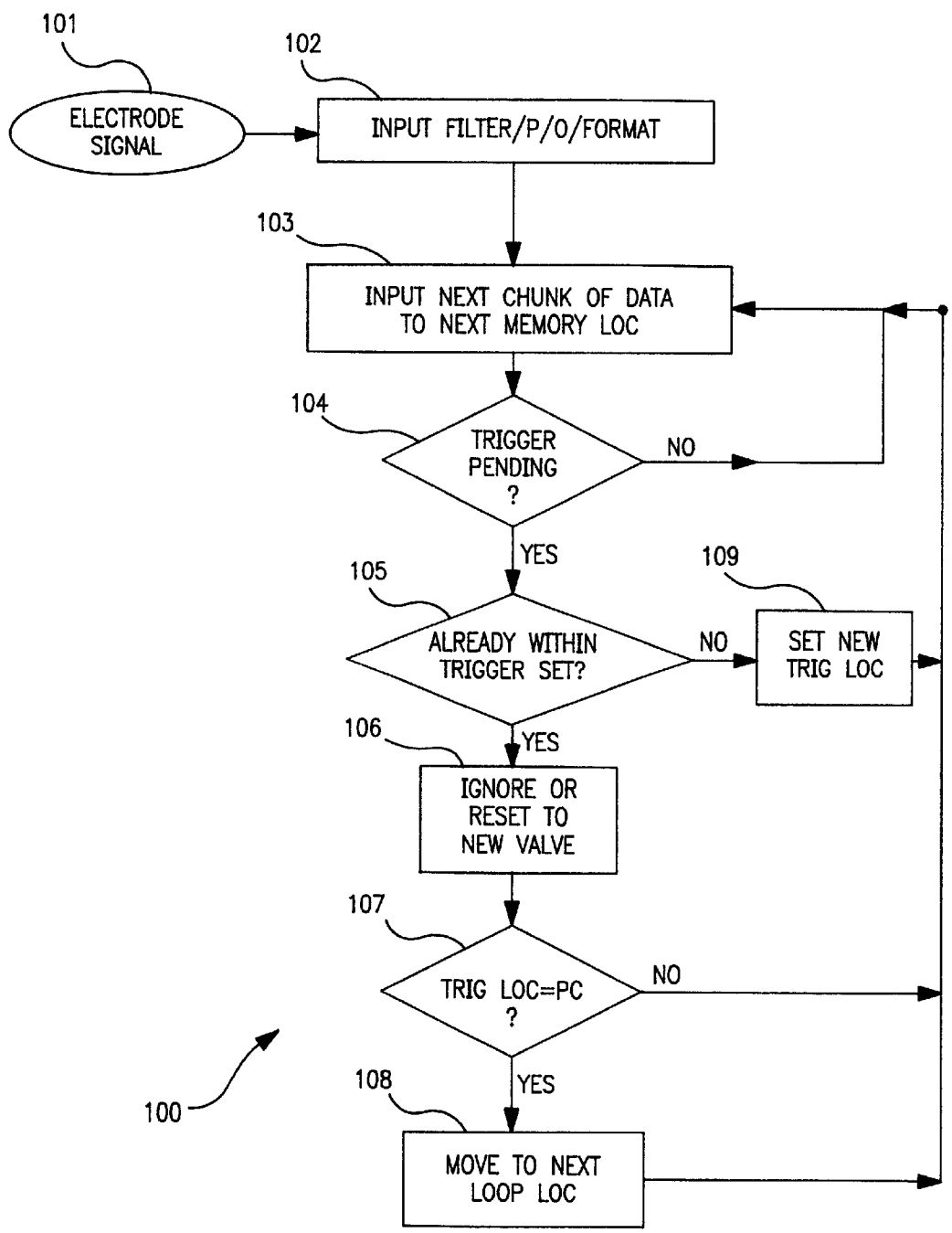
FIG. 12 is a flow chart of the functioning of the recordation of triggered events in a preferred embodiment of the invention.

The diagrammatic algorithm 100 to indicate the flow of this information is found in the illustration of FIG. 12 in which an electrode signal 101 is input filtered, converted from analog input to digital values, compressed and formatted if desired in step 102 so as to be in appropriate form to store in a memory location designated by a program counter pointer.

This data word's form could be containing a value representing input signal compressed at various available ratios, and may be mixed with other information like data provided by another sensor or clock data. The data stored will of course carry information related to the signal taken at the sampling rate. Thus lower sampling rates to save power will adversely affect the usefulness or detail of the data. Whatever its preferred form, each data point stored as a word is referred to as a chunk.

Output form step 102 provides the next chunk of data to the next memory location in step 103.

Device checks to see if there is any trigger pending after storing each chunk of data in step 104. If not, the next chunk of data is stored. If there is, the device preferably checks to see if there is another trigger already set and if so either ignores it or resets the value of the reserved looping memory area (like areas 111a–d in FIG. 11) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

It should be recognized that any of the inventive concepts taught herein may be applied to implantable devices to supplement their other functions, such as a supplemental recording system for a pacemaker, implantable drug pump, et cetera. Further, known enhancements to telemetric communication can be used to automatically activate off-loading of data to a device located in the patient's home. Such a device could send its received communications to the attending care giver/physician's office at some convenient time, telephonically or otherwise so as to enable close compliance with prescribed follow-up of patient conditions. This invention is not understood to be limited in scope except by the following claims.

What is claimed is:

1. An implantable medical device for sensing electrocardiograms in the far field having a memory in a housing for storing said far field ECGs, comprising;

electrodes outside said housing of said implantable medical device, for use in the far field, sense amplifier and QRS detector circuit in said housing, connected to said electrodes for sensing apparent R-waves and for issuing an apparent R-wave detection signal when a predetermined characteristic of a QRS complex is detected by said detector circuit, accommodation period processing circuit connected to receive said detection signals from said detector circuit, for initiating and timing until it expires, an accommodation period after said processing circuit receives a said detection signal, and for extending said accommodation period if a next detection signal is received from said detector circuit during an accommodation period, but for passing an R-wave detected signal if said next detection signal is received after an accommodation period has expired, and a trigger circuit, for receiving said passed signals from said processing circuit and for initiating and timing until it expires, a pending trigger period, wherein if a predetermined number of passed signals is received by said trigger circuit when said trigger period expires, said trigger circuit triggers stores into said memory a segment of said far field ECG.

2. The implantable medical device as set forth in claim 1, wherein said trigger circuit restarts said trigger period if less than a predetermined number of passed signals are received during a substantial portion of said pending trigger period.

3. The implantable medical device as set forth in claim 1, wherein said trigger circuit restarts said pending trigger period if more than a predetermined number of passed signals are received during a substantial portion of said pending trigger period.

4. The implantable medical device of claim 1, wherein said trigger circuit times a plurality of pending trigger periods, and wherein said trigger circuit restarts at least one of said plurality of pending trigger periods if less than a predetermined number of passed signals are received during a substantial portion of said at least one of said pending trigger period, and restarts another of said pending trigger periods if more than a predetermined number of passed signals are received during a substantial portion of said another of said pending trigger periods.

5. The implantable medical device of claim 1 further comprising an accommodation extension monitoring circuit for monitoring said accommodation processing circuit activity and comparing a total accommodation and extension period to at least one predetermined value to determine if the accommodation period has been extended beyond said at least one predetermined value.

6. The implantable medical device of claim 1 further comprising a denial period circuit connected to receive apparent R-wave detection signals from said sense amplifier and QRS detector circuit, and for establishing a pending denial period during which no said apparent R-wave detection signals can be passed to said trigger circuit.

7. An implantable medical device as set forth in claim 1 and further comprising a denial period circuit connected to receive apparent R-wave detection signals from said sense amplifier and QRS detector circuit, and for establishing a pending denial period during which no said apparent R-wave detection signals can be acted upon by said trigger circuit.

8. An implantable medical device of claim 1 further comprising a manual activation circuit for receiving manual activation signals and storing ECG segments in said memory, responsive thereto.

9. The implantable medical device of claim 1 further comprising a second trigger circuit comprising a sensor circuit producing a sensor circuit output, the value of which is dependent on a physiologic measurement made by said sensor, and a sensor interpreter circuit for storing ECG segments in said memory based on said sensor output, responsive to a predetermined physiologic measurement value being indicated in said sensor circuit output.

10. The implantable medical device of claim 1 further comprising a second trigger circuit comprising a sensor circuit producing a sensor circuit output, the value of which is dependent on a physiologic measurement made by said sensor, and a sensor interpreter circuit for storing a signal value representative of said sensor circuit output in said memory based on said sensor output, responsive to a predetermined physiologic measurement value being indicated in said sensor circuit output.

11. The implantable medical device of claim 10 wherein said memory is divided into segments having series of locations within each segment and wherein said signal value representative of said sensor circuit output and said ECG segment are stored together in a series of memory locations in a segment of said memory.

12. The implantable medical device of claim 9, further comprising yet another sensor circuit, wherein said yet another sensor circuit is for sensing a physiological parameter and from said sensing producing a yet another physiologic signal value and wherein said second trigger circuit storing a signal value representative of said physiologic sensor circuit output also causes storage of said yet another physiologic signal value into said memory.

13. The implantable medical device of any of claims 9–12, wherein said second trigger circuit is responsive to sudden movements in location of said implantable medical device so as to produce said predetermined measurement value in situations similar to falling.

14. An implantable medical device comprising:
a program controlled microprocessor circuit operating under program control, said program stored in a memory circuit and both circuits within a housing,
an electrode pair for receiving cardiac electrogram signals in a far field and for providing said electrogram signals to an input amplifier and R-wave sensing circuit, said sensing circuit for generating an R-wave sensed output signal when an R-wave is sensed, said R-wave sensed output signal being monitorable by said microprocessor circuit, and said sensing circuit for producing an amplitude output useable by an analog to digital converter circuit,
said analog to digital converter circuit operative at a sampling rate to produce a signal representing one value in a range of digital values related to an amplitude of said amplitude output for each said amplitude output, and to do so on a continuous basis, and wherein,
said program controlled microprocessor circuit is operated to store a series of said analog to digital converter output signals representative of a segment of said electrogram signals in said memory responsive to receiving a predetermined number of R-wave sensed outputs within a trigger time, but excluding from consideration any R-wave sensed outputs received within a denial time in determining whether said predetermined number of R-wave sensed outputs has been received within said trigger time, said denial time being of a fixed duration and initiating on the receiving of an R-wave sensed output not within a previous denial time.

15. The implantable medical device of claim 14 wherein said program controlled microprocessor circuit is also operated to exclude from consideration any R-wave sensed outputs received by said microprocessor within an accommodation period, said accommodation period running for a predetermined length of time and initiated by an R-wave sensed output received outside any previously initiated accommodation period, and further, if an R-wave sensed output has been received within said accommodation period, extending said accommodation period.

16. The implantable medical device of claim 14 wherein if said accommodation period is extended for more than an accommodation limit period, said program controlled microprocessor circuit is also operated to discontinue further accommodation extension.

17. A method for recording far field cardiac ECGs in an implantable medical device comprising:
a) employing an implanted medical device for monitoring said ECG signal in the far field,
b) determining when an apparent R-wave is sensed in the far field by said implanted medical device,
c) setting a first accommodation period to run from after said R-wave is sensed,
d) running said first accommodation period, and
e) if a next apparent R-wave is determined to have been sensed while running said first accommodation period, extending said first accommodation period, but
f) if said next apparent R-wave is sensed after said first accommodation period, employing said next apparent R-wave for determining whether to initiate the storage of a segment of said ECG.

18. The method of claim 17 further comprising:
g) if said accommodation period has been extended,
h) determining if said accommodation period has been extended beyond a predetermined acceptable length, and if it has been extended beyond said predetermined acceptable length, terminating further extension and returning to step (b).

19. The method of claim 17, further comprising:
an intermediate step of setting and running a denial period which expires before the first accommodation period starts, and wherein step (e) further comprises ignoring any apparent R-wave which occurs during the running of the denial period.

20. A method for recording far field cardiac ECGs in an implantable medical device comprising:
   a) employing an implanted medical device for monitoring said ECG signal in the far field,
   b) determining when an apparent R-wave is sensed in the far field by said implanted medical device,
   c) setting a first accommodation period to run from after said R-wave is sensed,
   d) running said first accommodation period, and
   e) if a next apparent R-wave is determined to have been sensed while running said first accommodation period, ignoring said next apparent R-wave, but
   f) if said next apparent R-wave is sensed after said first accommodation period, employing said next apparent R-wave for determining whether to initiate the storage of a segment of said ECG.

* * * * *